United States Patent
Pirkl et al.

(10) Patent No.: US 7,495,124 B2
(45) Date of Patent: Feb. 24, 2009

(54) PROCESS FOR THE PRODUCTION OF VERY PURE 2,4'-METHYLENEDIPHENYL DIISOCYANATE

(75) Inventors: Hans-Georg Pirkl, Leverkusen (DE); Jeffrey Bolton, Baytown, TX (US); Walter Meckel, Düsseldorf (DE); Ulrich Wolf, Kerken (DE); Matthias Wintermantel, Köln (DE); Jochen Mahrenholtz, Krefeld (DE)

(73) Assignee: Bayer MaterialScience AG, Leverkusen (DE)

( * ) Notice: Subject to any disclaimer, the term of this patent is extended or adjusted under 35 U.S.C. 154(b) by 488 days.

(21) Appl. No.: 11/048,172

(22) Filed: Feb. 1, 2005

(65) Prior Publication Data

US 2005/0222291 A1    Oct. 6, 2005

(30) Foreign Application Priority Data

Feb. 4, 2004   (DE) ................. 10 2004 005 319

(51) Int. Cl.
*C07C 263/20*   (2006.01)
(52) U.S. Cl. .............. 560/352; 560/347; 560/358; 560/359; 528/80; 528/85; 203/71
(58) Field of Classification Search ............ 560/352, 560/347, 358, 359; 528/80, 85; 203/71
See application file for complete search history.

(56) References Cited

U.S. PATENT DOCUMENTS

| 4,189,354 | A |   | 2/1980  | Ellendt et al. |
|-----------|---|---|---------|----------------|
| 4,189,443 | A |   | 2/1980  | Eifler et al. |
| 4,414,074 | A |   | 11/1983 | Ellendt et al. |
| 4,597,909 | A |   | 7/1986  | Keggenhoff et al. |
| 4,719,278 | A | * | 1/1988  | Wellner et al. ............... 528/64 |
| 5,179,227 | A |   | 1/1993  | Ishida et al. |
| 5,284,882 | A | * | 2/1994  | Rossio et al. ............... 521/137 |
| 6,096,238 | A |   | 8/2000  | Lutter et al. |
| 2004/0171869 | A1 |   | 9/2004 | Reif et al. |

FOREIGN PATENT DOCUMENTS

| CA | 1097690   | 3/1981  |
| CA | 1 137 514 | 12/1982 |
| EP | 431 331   | 5/1993  |
| GB | 1 263 439 | 2/1972  |
| GB | 1 517 162 | 7/1978  |
| WO | 93/09158  | 5/1993  |

* cited by examiner

*Primary Examiner*—John Cooney
(74) *Attorney, Agent, or Firm*—Noland J. Cheung; Lyndanne M. Whalen; N. Denise Brown

(57) ABSTRACT

The present invention relates to a process for the production of MDI fractions containing 2,4'-MDI, and in which the 2,2'-MDI component from the MDA production is largely removed from the isomer mixture. Highly reactive monomeric MDI products can be produced in this way. These MDI products are characterised in their processing by significantly reduced emissions of MDI monomers.

18 Claims, No Drawings

PROCESS FOR THE PRODUCTION OF VERY PURE 2,4'-METHYLENEDIPHENYL DIISOCYANATE

BACKGROUND OF THE INVENTION

The present invention relates to a process for the production of diisocyanates of the diphenylmethane series with very high contents of 2,4'-methylenediphenyl diisocyanate, and to a process for the production of prepolymers and polymers from these diisocyanates.

Aromatic isocyanates are important raw materials for the production of polyurethane materials. In this connection the diisocyanates and polyisocyanates of the diphenylmethane series (MDI) play the greatest role, quantitatively.

Polyisocyanates of the diphenylmethane series are understood to denote isocyanates and isocyanate mixtures of the following type:

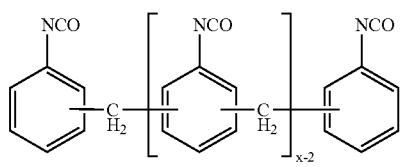

x = 2 to n where n denotes a natural number >2.

Similarly, polyamines of the diphenylmethane series are understood to denote compounds and compound mixtures of the following type:

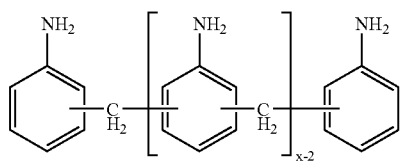

x = 2 to n where n denotes a natural number >2.

It is known that diisocyanates and polyisocyanates of the diphenylmethane series (MDI) are produced by phosgenation of the corresponding diamines and polyamines of the diphenylmethane series (MDA). The diamines and polyamines of the diphenylmethane series (MDA) are themselves produced by condensation of aniline and formaldehyde. The corresponding diisocyanates, 2,2'-MDI, 2,4'-MDI and 4,4'-MDI, which are described in the specialist circles as 2-ring (i.e. bi-nuclear) compounds of MDI (i.e. diisocyanates of the diphenylmethane series), are obtained by phosgenation of diamines of the diphenylmethane series. During the condensation of aniline and formaldehyde, the 2-ring i.e. (bi-nuclear) MDA (methylenediphenyldiamine), however, also continues to react further with formaldehyde and aniline to form higher-nuclear (i.e. poly-nuclear or poly-ring) MDA types, which after the phosgenation constitute the polynuclear content in the polymeric MDI (i.e. polyisocyanates of the diphenylmethane series).

The crude MDI mixture produced in the phosgenation can be separated in the polymer/monomer separation by means of simple evaporation or distillation into 2-nuclear-MDI (i.e. monomeric MDI) and a polymer-MDI fraction (i.e. polymeric MDI or PMDI). The isomer mixture of the 2-nuclear-MDI fraction contains, in addition to the diisocyanates 2,2'-MDI, 2,4'-MDI and 4,4'-MDI, some secondary components such as solvent residues or phenylisocyanate derivatives. The monomeric 2-nuclear-MDI fraction is separated, according to the prior art, by distillation or by crystallisation into the 4,4'-MDI isomers and into a mixture comprising about 50% 2,4'-MDI and 50% 4,4'-MDI. The two monomeric products are then supplied as polyurethane raw material to the world market, or they are processed further with polymeric MDI into mixed products.

At the present time, very pure 2,4'-MDI is not available commercially in large-scale amounts. This has not changed despite the fact that many positive properties of 2,4'-MDI have recently become known. Thus, in polyurethane flexible foam systems, for example, a 2,4'-MDI can replace the conventional TDI system of 2,4-TDI and 2,6-TDI (as described in EP-B1 0676434). Also, 2,4'-MDI can be successfully used in heat-curable one-component polyurethane systems (as described in EP-B1 0431331).

The 4,4'-isomer of MDI is the most important MDI isomer on account of its high reactivity and its extremely good ability to form hard segments. By comparison, the 2,4'-isomer, on account of its different reactivity, is characterised, in particular, by use in very low viscosity, relatively low monomer content prepolymers.

Thus, WO-A 93/09158 describes prepolymers with low monomer contents. By reacting isocyanates and polyethers containing secondary hydroxyl groups, at NCO/OH ratios of 1.6 to 1.8, and when using variously reactive NCO groups in the isocyanate molecule, results in low monomer content prepolymers. Monomeric MDI with a content of 92 wt. % of 2,4'-diisocyanatodiphenylmethane is given as an example of a suitable isocyanate. Important areas of use are adhesives and coatings, and, in particular, film composite systems with low migration values.

One application of diphenylmethane diisocyanates is in the production of film composites, which are employed in the foodstuffs packaging sector. The hygienically satisfactory, cheap packaging of foodstuffs guaranteeing a high storage stability is nowadays achieved with composite films. These composite films are formed by bonding films with different barrier properties such that the composite can optimally be adjusted to the respective requirements.

Polyurethanes represent the adhesives of choice. These adhesives are used in solvent-containing and solvent-free form. Due to the trend towards solvent-free systems, two-component systems consisting of a polyol mixture and a prepolymer based on isocyanates have become increasingly popular. Due to the traces of moisture adsorbed on the film surfaces, it has proved necessary to employ adhesives with a relatively large excess of isocyanate groups compared to OH groups.

This large excess of isocyanates also constitutes, however, a limiting factor in the further processing of the film composites, since the film composites must be free of aromatic amines before they can come into contact with foodstuffs.

Therefore, before the composite films can be processed further, they must be stored until amines are no longer detectable. This time period depends on many factors, such as, for example, the properties of the employed adhesive, the nature of the films (e.g. type and thickness), and the prevailing temperature and atmospheric humidity. In this regard, the presence of aromatic amines in the test foodstuffs can presumably be explained by the fact that monomeric isocyanates that have not fully reacted migrate through the thin films and slowly react with moisture on the surface to form polyureas, which are stable under normal storage conditions for foodstuffs. Until this reaction has gone to completion, any monomeric isocyanates that are present can also be partially hydrolysed to amines by the test foodstuffs used in the test.

Due to the much greater reactivity of the NCO group located in the 4-position compared to that of the NCO group located in the 2-position in MDI, MDI isomers with at least one NCO group located in the 4-position can be integrated significantly faster into an oligomeric or polymeric polyurethane network, and can thus be prevented from migrating through the film. Accordingly, the concentration of still free, unbound monomeric MDI isomers with NCO groups located in the 4-position (i.e. 4,4'-MDI and 2,4'-MDI) falls rapidly after production of an MDI prepolymer, and in the processing of this MDI prepolymer with polyols. Due to its significantly lower reactivity, the 2,2'-MDI on the other hand remains longer in monomeric form in the adhesive layer than the other MDI isomers, and can therefore, take longer to migrate through the film. Accordingly, the content of 2,2'-MDI in the MDI isomer mixture is a critical quantity and should be as low as possible.

The following information is also known from the prior art regarding the production of MDI.

The production of MDI mixed products that contain the various MDI isomers, by a specific synthesis of the MDA containing the corresponding MDA isomer, is known and described in the literature. EP-B1 158059 discloses the production of a particularly high 2-nuclear content in an MDA mixture containing ca. 80% 4,4'-MDA and ca. 10% 2,4'-MDA with a 2-nuclues content of ca. 90%. On the other hand, the yield of 2,4'-MDA can be purposefully increased, as is disclosed in EP-B1 3303 with an MDA which contains 88 wt. % of 2-nuclear MDA with 19 wt. % of 2,2'-MDA, 36 wt. % of 2,4'-MDA and 45 wt. % of 4,4'-MDA. In particular, the production of monomer-rich MDA types containing a large content of 2,4'-MDA generally leads to a large amount of 2,2'-MDA as by-product. On account of its lack of reactivity, the 2,2'-MDI formed from the resulting 2,2'-MDA is, however, undesirable in large concentrations in many applications.

The production of high polymer content MDA with 2-nuclear contents of from 46% to 65% is described in, for example, DE-A1 2750975 and DE-A1 2517301.

The essential parameters by means of which the proportion of 2,4'-MDA can be adjusted in the condensation of aniline and formaldehyde are known. As a rule, the content of 2-nuclear MDA is adjusted by the excess of aniline in the condensation. The proportion of 2,4'-MDA present in the 2-nuclear MDA can be adjusted by a low degree of protonation during the condensation, or in other words, by a low molar ratio of HCl: aniline such as, for example, <0.2:1, or by a high reaction temperature, as described in DE-A1 3407494.

The large-scale production of isocyanates by reacting the corresponding amines with phosgene in solvents is known and is described in detail in the literature (Ullmanns Enzyklopädie der technischen Chemie, 4$^{th}$ Edition, Vol. 13, pp. 347-357, Verlag Chemie GmbH, Weinheim, 1977). The MDA phosgenation leads first of all to a crude MDI mixture. Also, the production of monomeric MDI and polymeric MDI from the crude MDI mixture by distillation or crystallisation is, in principle, known in the relevant literature.

Basically, two main products are isolated according to the prior art from the crude monomeric 2-nuclear MDI fraction of the originally crude MDI mixture. The first of the two main products of the isomer separation is a 4,4'-MDI-rich isomer mixture ("4,4'-product"), which is practically free from 2,2'-MDI and which also contains <3 wt. % of 2,4'-MDI. The second of the two main products of the isomer separation is a 2,4'-MDI-rich mixture ("2,4'/4,4'-product"), which contains from 20 to 70 wt. % of 2,4'-MDI and up to 3 wt. % of 2,2'-MDI, with the remainder being 4,4'-MDI. To produce these two main products, the following two industrial processes starting from the crude monomeric 2-nuclear MDI fraction that was obtained from the crude MDI mixture from the polymer/monomer separation are, as a rule, used at the present time:

a) distillation, as described in, for example, DE-A1 3145010 and/or DE-A1 2631168;

or b) crystallisation, as described in, for example, EP-A2 482490 and/or DE-A 2532722.

Specialist in the polyurethane and polyisocyanate fields are presently concentrating on the most economical production process of the monomeric isomer mixtures, of the "4,4'-product" and of the "2,4'/4,4'-product" (M. Stepanski, P. Faessler: "New hybrid process for purification and separation of MDI isomers", Sulzer Chemtech, Presentation at the Polyurethane Conference 2002 in Salt Lake City, October 2002).

The production of relatively highly concentrated 2,4'-MDI starting from an MDA mixture with high contents of 2,4'-MDA that was obtained by condensation of aniline and formaldehyde, with a low degree of aniline protonation, is described in, for example, WO-A1 02/070581. A purification involving the removal of 2,2'-MDI from the 2,4'-MDI that is obtained is not envisaged in the process according to WO-A1 02/070581. However, particularly in the production of 2,4'-rich MDA mixtures with a low degree of protonation, i.e. with a low ratio of HCl to aniline, disproportionately large amounts of 2,2'-MDA are formed. This is described in, for example, EP-B1 3303. These large amounts of 2,2'-MDA or 2,2'-MDI, respectively have to be removed at least partially after phosgenation and before the mixtures are used in the polyurethane production. In fact, however, the purity of the 2,4'-MDI with respect to quantity of 2,2'-MDI present is an essential quality feature that is even more important than the purity with respect to 4,4'-MDI.

The process described in WO-A1 02/070581, in which an MDI mixture with a high content of 2,4'-MDI is produced by phosgenation of a corresponding MDA mixture with a high content of 2,4'-MDA, corresponds to the conventional method described in the prior art for producing an MDI mixture containing ca. 50 wt. % of 2,4'-MDI and ca. 50 wt. % of 4,4'-MDI. Since 2,4'-MDI is a low boiling point compound compared to 4,4'-MDI, 2,4'-MDI is obtained as overhead product by distillation. The significant factor in this case is that further low boiling point compounds, and in particular 2,2'-MDI, accumulate in the overhead product. If 4,4'-MDI is separated from the 2,4'-fraction by conventional means, then there is obtained as a first product the first main product "4,4'-MDI product" already mentioned above, that generally contains about 1-2 wt. % of 2,4'-MDI, and in addition, as a second main product, the second main product "2,4'/4,4'-MDI product" also already mentioned above, which forms a mixture of 2,4'-MDI and 4,4'-MDI in the vicinity of the eutectic point. In this connection, the 2,2'-isomer on account of its boiling point accumulates in the eutectic mixture. A typical content of 2,2'-MDI in this eutectic mixture is between 0.8 and 5 wt. %.

A similar situation exists in the separation of "4,4'-MDI product" by crystallisation. In this case the 2,2'-isomer is necessarily concentrated with the 2,4'-rich fraction in the mother liquor. If the resultant mother liquor is now separated into the isomers 2,4'-MDI as distillate and 4,4'-MDI in the bottom of a distillation column, the undesired and unreactive 2,2'-MDI likewise accumulates in the desired 2,4'-MDI fraction. Thus, depending on the initial quality of the crude 2-nuclear MDI fraction, a 2,4'-MDI containing 0.8 to 5 wt. % of 2,2'-MDI is obtained. Furthemore, low boiling point secondary components such as phenyl isocyanates and traces of solvents can pass into the distillate, if these are not initially removed from the starting mixture.

If, on the other hand, an attempt is made to separate the resultant mother liquor containing the isomers 2,4'-MDI and 4,4'-MDI by crystallisation, then first of all the eutectic point must be exceeded using a non-crystallisation process in order not to obtain only pure 4,4'-MDI crystallisate and a 2,4'-containing mother liquor with high contents of 4,4'-MDI. For this reason, no highly enriched 2,4'-MDI can be obtained by a pure crystallisation process starting from the crude 2-nuclear MDI fraction. The eutectic point may be exceeded, for example, by a distillation process as described above. In this case, the process disclosed in the present patent application for the production of very pure 2,4'-MDI fractions can alternatively be carried out in step d) using a crystallisation process for separating the major proportion of 4,4'-MDI.

In DE-A 2631168, a process is described for the production of MDI mixtures with low contents of residual chlorine using distillation methods. According to the process described in DE-A-26 31 168, MDI mixtures containing 2,4'-MDI in an amount of more than 97 wt. % and having less than 50 ppm of chlorine can also be produced in this way.

The large content of 2,2'-MDI interferes in practically all end-use applications and areas since it is unreactive and can be completely incorporated into a polymer network only under drastic reaction conditions. In most cases, significant amounts of 2,2'-MDI remain as residual monomer in the processing and are possibly released over time, or they react in a random manner with atmospheric moisture and lead to impaired polymer properties. Also, residual traces of solvents are undesirable in the polyurethane production and these adversely affect the product quality due to their unpleasant smell. Traces of phenyl isocyanates that are possibly contained in turn act as chain terminators in the polyurethane reaction and also adversely affect the polymer properties.

SUMMARY OF THE INVENTION

The object of the present invention is to provide a process for the production of MDI isomer mixtures with high contents of 2,4'-MDI, while reducing the amounts of components such as 2,2'-MDI, solvent residues and phenyl isocyanates to a level such that these no longer that interfere in the production of polyurethanes.

The invention relates to a process for the production of a fraction of diisocyanates of the diphenylmethane series containing at least 99 wt. % of 2-nuclear methylenediphenyl diisocyanate, based on the total weight of the fraction. This process comprises
a) reacting aniline and formaldehyde in the presence of an acid catalyst to form diamines and polyamines of the diphenylmethane series which contain 2-nuclear methylenediphenyldiamine,
b) phosgenating the 2-nuclear methylenediphenyldiamine containing diamines and polyamines of the diphenylmethane series, optionally in the presence of a solvent, thereby forming a crude diisocyanate and polyisocyanate,
c) separating a fraction containing at least 95 wt. % of 2-nuclear methylenediphenyl diisocyanate with a content of 4,4'-MDI of from 49 to 95.99 wt. %, a content of 2,4'-MDI of from 4 to 45 wt. % and a content of 2,2'-MDI of from 0.01 to 20 wt. %, based on the total weight of the fraction, from the crude diisocyanate and polyisocyanate formed in step b),
d) optionally, removing 4,4'-MDI in an amount of from 10 to 98% from the fraction obtained in step c),
e) separating, either wholly or partially, 2,2'-MDI from the fraction obtained in step c) or in step d), thereby forming a fraction containing from 0 to 0.4 wt. % of 2,2'-MDI, from 1 to 95 wt. % of 4,4'-MDI and from 5 to 98.6 wt. % of 2,4'-MDI, based on the total weight of the MDI isomers, and optionally in a preferred embodiment
f) separating a fraction containing at least 99 wt. % of 2-nuclear methylenediphenyl diisocyanate, based on the total weight of the fraction, which contains from 0 to 0.5 wt. % of 2,2'-MDI, from 0.1 to 80 wt. % of 4,4'-MDI and from 20 to 99.9 wt. % of 2,4'-MDI, based on the total weight of MDI isomers, from the fraction formed in e) which contains from 0 to 0.4 wt. % of 2,2'-MDI, from 1 to 95 wt. % of 4,4'-MDI and from 5 to 98.6 wt. % of 2,4'-MDI, based on the total weight of the MDI isomers.

The essence of the invention is a process for the targeted removal of 2,2'-MDI, as well as solvent residues and phenyl isocyanates, from the monomeric isomer mixture by a separation process, and in particular by distillation. Since phenyl isocyanates, solvents such as monochlorobenzene and orthodichlorobenzene, as well as the 2,2'-MDI isomer have a lower boiling point compared to 4,4'-MDI and 2,4'-MDI, they steadily accumulate in the distillate from a column. In principle, however, crystallisation or extraction may also be used. The MDI mixtures produced and purified in accordance with the present invention which have a high content of 2,4'-MDI can be used extremely effectively in the polyurethane production.

DETAILED DESCRIPTION OF THE INVENTION

The polyamine or polyamine mixture of the diphenylmethane series used in the process according to the invention are formed in step a) by condensing aniline and formaldehyde in the presence of an acid catalyst. This is known and described by, for example, H. J. Twitchett, Chem. Soc. Rev. 3(2), 209 (1974); W. M. Moore in: Kirk-Othmer Encycl. Chem. Technol., $3^{rd}$ Ed., New York, 2, 338-348 (1978). For the process in accordance with the present invention, it is not important whether aniline and formaldehyde are first of all mixed in the absence of the acid catalyst and the acid catalyst is then added, or whether a mixture of aniline and acid catalyst is reacted with formaldehyde.

Suitable polyamine mixtures of the diphenylmethane series are conventionally obtained by condensation of aniline and formaldehyde in a quantitative molar ratio of from 20:1 to 1.6:1, preferably from 10:1 to 1.8:1, as well as a quantitative ratio of aniline to acid catalyst of from 20:1 to 1:1, preferably from 10:1 to 2:1.

Formaldehyde is normally used as aqueous solution on an industrial scale. In this connection, the water content may vary from 1 to 95% by wt., based on the total weight of the solution. An aqueous solution containing from 50 to 80% by wt. of water (based on the total weight of the solution) is preferably used. However, other compounds supplying methylene groups, such as, for example, polyoxymethylene glycol, para-formaldehyde or trioxane, may also be used.

Strong organic acids, and preferably inorganic acids, have proved suitable as acid catalysts for the reaction of the aniline and formaldehyde. Suitable acids include, for example, hydrochloric acid, sulfuric acid, phosphoric acid and metanesulfonic acid. Hydrochloric acid is preferably used. Solid acid catalysts such as, for example, organic and inorganic ion exchangers, acid silicon/aluminum mixed oxides as well as, preferably, acid zeolites may, however, also be used.

In a preferred embodiment of the process, aniline and the acid catalyst are first of all mixed together. This mixture is mixed in a suitable manner, optionally after the removal of heat, in a further step with formaldehyde at temperatures between about 20° C. and 100° C., preferably about 30° C. and 70° C., and then subjected to a preliminary reaction in a suitable residence time apparatus. The preliminary reaction is carried out at temperatures between about 20° C. and 100° C., preferably in the temperature range of from about 30° C. to about 80° C. On completion of the mixing and preliminary reaction, the temperature of the reaction mixture is raised either in stages or continuously, and optionally under excess pressure, to a temperature of from about 100° C. to about 250° C., preferably to a temperature of from about 100° C. to about 180° C., particularly preferably to a temperature of from about 100° C. to about 160° C.

It is, however, also possible in another embodiment of the process, to mix and react aniline and formaldehyde first of all in the temperature range of from about 5° C. to about 130° C., preferably from about 40° C. to about 100° C., and particularly preferably from about 60° C. to about 90° C., in the absence of the acid catalyst. In this case, condensation products of aniline and formaldehyde are formed (so-called aminal). On completion of the aminal formation, water present in the reaction mixture may be removed by phase separation or by other suitable procedures Such as, for example, by distillation. The condensation product is then mixed in a suitable way with the acid catalyst in a further process step, and it undergoes a preliminary reaction at a temperature of about 20° C. to about 100° C., preferably of about 30° C. to about 80° C., in a residence time apparatus. The temperature of the reaction mixture is then raised in stages or continuously, and optionally under excess pressure, to a temperature of about 100° C. to about 250° C., preferably of about 100° C. to about 180° C., and particularly preferably to a temperature of about 100° C. to about 160° C.

In order to work up the acid reaction mixture, the reaction mixture is neutralised as described in the prior art with a base. According to the prior art, the neutralisation is normally carried out at temperatures of, for example, from 90° to 100° C. (see H. J. Twitchett, Chem. Soc. Rev. 3(2), 223 (1974)). Suitable as bases include, for example, the hydroxides of the alkali metals and alkaline earth metals. NaOH (i.e. sodium hydroxide) is preferably used to neutralise the reaction mixture.

After the neutralisation, the prior art discloses that the organic phase is separated from the aqueous phase by suitable methods (e.g. phase separation in a separating flask). This separation of organic and aqueous phases may take place at the same temperature at which the neutralisation of the acid rearrangement mixture took place. The product-containing organic phase remaining after the separation of the aqueous phase is subjected to a wash procedure in order to separate salts and excess base. This wash procedure is also described in the prior art. The purified organic phase is then freed from excess aniline and other substances present in the mixture (e.g. further solvents) by suitable physical separation methods, such as for example distillation, extraction or crystallisation.

The polyamine of the diphenylmethane series (crude MDA) thus obtained from step a) is reacted in step b), according to known methods, with phosgene, optionally in an inert organic solvent, to form the corresponding isocyanates. The molar ratio of crude MDA to phosgene is conveniently adjusted such that there are from 1 to 10 moles, and preferably 1.3 to 4 moles of phosgene are present in the reaction mixture, per mole of $NH_2$ group present in the reaction mixture. Suitable inert solvents include chlorinated, aromatic hydrocarbons such as, for example, monochlorobenzene, dichlorobenzenes, trichlorobenzenes, the corresponding toluenes and xylenes, as well as chloroethylbenzene. Monochlorobenzene, dichlorobenzene or mixtures of these chlorobenzenes may in particular be used as inert organic solvents. The amount of solvent is preferably adjusted so that the reaction mixture has an isocyanate content of between 2 to 40 wt. %, preferably between 5 and 20 wt. %, based on the total weight of the reaction mixture. The reaction of crude MDA with phosgene is, in this connection, carried out at temperatures of from 50° to 250° C., and at pressures ranging from ambient pressure up to 50 bar. The reaction is preferably carried out at a temperature of from 70° to 180° C. and at a pressure of from 2 to 20 bar.

After completion of the phosgenation step, the excess phosgene, any inert organic solvent, the HCl formed and/or mixtures thereof, are separated from the reaction mixture by suitable methods (e.g. by distillation). For this, the pressure is reduced stepwise to create a vacuum and the remaining excess phosgene and the HCl formed are evaporated and separated. The solvent is then reduced stepwise, preferably by evaporation, with further reduction of the absolute pressure down to 1 mbar, preferably down to 5 mbar. At the same time, the temperature is raised until the solvent is almost completely removed, down to a concentration of far less than 0.1%. Finally a crude diisocyanate and polyisocyanate (crude MDI mixture) is obtained in this step b).

A fraction containing at least 95 wt. % of 2-nuclear methylenediphenyl diisocyanate with a content of 4,4'-MDI of from 49 to 95.99 wt. %, a content of 2,4'-MDI of from 4 to 45 wt. % and a content of 2,2'-MDI of from 0.01 to 20 wt. %, based on the total weight of the fraction, is then separated from the crude diisocyanate and polyisocyanate in the polymeric/monomeric separation in step c). The separation of this 2-nuclear MDI fraction (i.e. monomieric MDI) preferably takes place in one stage or two stages. The lower boiling point fraction with high contents of 2-nuclear MDI isomers is evaporated overhead and removed, preferably by heating at temperatures of from 170° to 230° C. and at absolute pressures of from 0.1 to 30 mbar. Preferably the temperatures are from 180° to 220° C. and the absolute pressures are from 1 to 15 mbar.

Preferably, the fraction separated in step c) contains from 98 to 100 wt. % of 2-nuclear methylenediphenyl diisocyanate (based on the total weight of the fraction), with a content of 4,4'-MDI of from 80 to 93.9 wt. %, a content of 2,4'-MDI of from 6 to 19.9 wt. % and a content of 2,2'-MDI of from 0.1 to 5 wt. %, based on the total weight of the fraction. It is particularly prefered that the fraction separated in step c) contains at least 99 wt. % of 2-nuclear methylenediphenyl diisocyanate with a content of 4,4'-MDI of from 82 to 92.8 wt. %, a content of from 2,4'-MDI of 7 to 17.8 wt. % and a content of 2,2'-MDI of from 0.2 to 3 wt. %, based on the total weight of the fraction.

The isomer 4,4'-MDI is the MDI isomer most commonly used in the production of polyurethane. For this reason, it may be expedient first of all to separate to a large extent the 4,4'-MDI from the fraction obtained in step c). Preferably, from 10 to 98 wt. % of the 4,4'-MDI, more preferably from 50 to 95 wt. % and most preferably from 75 to 93 wt. % of the 4,4'-MDI is therefore separated in a distillation step or a crystallisation step in step d). This separation or removal of the 4,4'-MDI in step d) from the fraction obtained in step c) is, however, optional. The distillation column employed in step d) is preferably operated at a temperature of from 170° to 230° C. and at absolute pressures of from 0.1 to 30 mbar. It is particularly preferred that the stream enriched with 4,4'-MDI is withdrawn from the bottom of the distillation column, with conditions being adjusted such that temperatures range from 180° to 220° C. and absolute pressures range from 1 to 15 mbar. Step d) may alternatively be carried out by means of one or more crystallisation steps at temperatures of from 30° to 40° C., with the 4,4'-rich fraction occurring as crystallisate, and the 2,4'-rich fraction and 2,2'-rich fraction occurring as mother liquor. In this case preferably from 10 to 98 wt. %, more preferably from 50 to 95 wt. % and most preferably from 75 to 93 wt. % of the 4,4'-MDI are separated in step d) as crystallisate in the crystallisation.

Then, in step e), the 2,2'-MDI is then either wholly or partially separated from the fraction obtained in step c) which contains at least 95 wt. % of 2-nuclear methylenediphenyl diisocyanate with a content of 4,4'-MDI of from 49 to 95.99 wt. %, a content of 2,4'-MDI of from 4 to 45 wt. % and a content of 2,2'-MDI of from 0.01 to 20 wt. %, based on the total weight of the fraction. This whole or partial separation of the 2,2'-MDI may occur after the prior separation of large amounts of the 4,4'-MDI in optional step d).

The 2,2'-rich fraction obtained as distillate in step e) contains at least 99 wt. % of 2-nuclear MDI, and contains from 10 to 98 wt. % of 2,2'-MDI, from 2 to 90 wt. % of 2,4'-MDI as well as from 0 to 30 wt. % of 4,4'-MDI, based on the total weight of the MDI isomers. Preferably the 2,2'-MDI-rich fraction contains from 20 to 95 wt. % of 2,2'-MDI, from 5 to 80 wt. % of 2,4'-MDI as well as from 0 to 20 wt. % of 4,4'-MDI, and more preferably from 50 to 85 wt. % of 2,2'-MDI, from 15 to 50 wt. % of 2,4'-MDI as well as from 0 to 10 wt. % of 4,4'-MDI, based on the total weight of the MDI isomers. In this way, preferably from 50 to 99.9999% (i.e. 100%), more preferably from 65 to 99.99% and most preferably from 80 to 99.9% are removed as distillate stream in step e) from the overall amount of 2,2'-MDI that was introduced with the crude diisocyanate and polyisocyanate in the separation (e.g. distillation) in step c).

The 2,2'-MDI fraction separated in step e) is then separated in a further step by isomer distillation into a low boiling point fraction as well as a 2,2'-MDI-rich fraction. The interfering low boiling point compounds, such as derivatives of phenyl isocyanate, solvent constituents and other readily volatile secondary products from the MDA and MDI production, such as, for example, acridine, are removed overhead as distillate. For this purpose, a partial amount of the MDI, for example, from 5 to 30% of the feed, preferably from 10 to 20% of the feed, is used as entraining agent in the distillate stream. The resulting higher boiling fraction contains the majority of the MDI useful products. Similarly, the interfering low boiling point compounds can be separated as mother liquor from the MDI useful product in one or more crystallisation steps.

In this regard, an MDI isomer mixture with high contents of 2,2'-MDI of from 5 to 99.99 wt. %, preferably from 10 to 95 wt. %, more preferably from 20 to 90 wt. % and most preferably from 30 to 85 wt. %, based on the total weight of the MDI isomers, is obtained by distillative separation of interfering low boiling point compounds. These isomer mixtures with high contents of 2,2'-MDI of from 5 to 99.99 wt. % of 2,2'-MDI, from 0 to 50 wt. % of 4,4'-MDI and from 0.01 to 95 wt. % of 2,4'-MDI, and preferably from 10 to 95 wt. % of 2,2'-MDI, from 0.1 to 89.99 wt. % of 2,4'-MDI and from 0.01 to 50 wt. % of 4,4'-MDI, based on the weight of the MDI isomers, can then be reacted with polyethers or polyesters in known manner to form polyurethanes or prepolymers. Alternatively, these isomer mixtures with high contents of 2,2'-MDI can also be used in combination with other isocyanate products, including other MDI mixed products for the replenishment of the 2,2'-content and 2,4'-content, as well as for their processing with polyethers or polyesters to prepare polyurethanes or prepolymers.

The separation of the 2,2'-MDI takes place in step e) preferably in a distillation column containing at least 10, more preferably at least 15 and most preferably at least 20 theoretical plates in the stripping part of the column in order to minimise the content of 2,2'-MDI in the bottom of the column. To this end, reflux ratios (i.e. distillate reflux in the column/amount of distillate removed) of from 0.5 to 500 are adjusted at the head of the column. Preferably reflux ratios of from 2 to 100 are adjusted. The absolute operating pressure of such a column is adjusted to range from 0.5 to 30 mbar, preferably from 1 to 15 mbar.

Alternatively, a column may also be used in which the fraction depleted of 2,2'-MDI is removed in the side stream. In this case, the stripping part of the column between the feed point of the stream from step c) or step d) and the removal point of the depleted 2,2'-MDI product must have a separation efficiency of at least 10, preferably at least 15 and more preferably at least 20 theoretical plates. The low 2,2'-MDI content fraction may in this connection be removed, in either gaseous or liquid form from the bottom of the column. For this purpose, reflux ratios (i.e. distillate reflux in the column/amount of distillate removed) of from 0.5 to 500 are adjusted at the head of the column. Preferably reflux ratios of from 2 to 100 are employed. The absolute operating pressure of such a column is adjusted to range from 0.5 to 30 mbar, preferably from 1 to 15 mbar.

After separating the 2,2'-MDI, a fraction containing from 0 to 0.4 wt. % of 2,2'-MDI, from 1 to 95 wt. % of 4,4'-MDI and from 5 to 98.6 wt. % of 2,4'-MDI, based on the total weight of the MDI isomers, is obtained in step e).

Preferably, the fraction obtained in step e) contains from 0 to 0.3 wt. % of 2,2'-MDI, from 5 to 85 wt. % of 4,4'-MDI and from 15 to 95 wt. % of 2,4'-MDI, based on the total weight of the MDI isomers, and more preferably from 0 to 0.18 wt. % of 2,2'-MDI, from 7 to 75 wt. % of 4,4'-MDI and from 25 to 93 wt. % of 2,4'-MDI, based on the total weight of the MDI isomers. It is most preferred that the fraction obtained contains from 0 to 0.10 wt. % of 2,2'-MDI, from 30 to 70 wt. % of 4,4'--MDI and from 30 to 70 wt. % of 2,4'-MDI, based on the total weight of the MDI isomers. The desired 2,4'-rich fraction and 2,2'-depleted fraction may optionally already be removed as end product in this step, for example, by means of a partial condensation of the vapor above the bottom phase of the column, thereby allowing the separate fractionation in step f) to be omitted. This may be a preferred embodiment for the production of a 2,2'-depleted eutectic mixture of 2,4'-MDI/4,4'-MDI with from 0 to 0.40 wt. % of 2,2'-MDI, from 30 to 70 wt. % of 4,4'-MDI and from 30 to 70 wt. % of 2,4'-MDI, based on the total weight of the MDI isomers, and preferably with from 0 to 0.20 wt. % of 2,2'-MDI, from 35 to 60 wt. % of 4,4'-MDI and from 40 to 65 wt. % of 2,4'-MDI, based on the total weight of the MDI isomers.

Optionally in a preferred embodiment, in step f), a fraction containing at least 99 wt. % of 2-nuclear MDI, based on the total weight of the fraction, and which contains from 0 to 0.5 wt. % of 2,2'-MDI, from 0.1 to 80 wt. % of 4,4'-MDI and from 20 to 99.9 wt. % of 2,4'-MDI, based on the total weight of the MDI isomers, is finally separated by distillation from the fraction obtained in step e) that contains from 0 to 0.4 wt. % of 2,2'-MDI, from 1 to 95 wt. % of 4,4'-MDI and from 5 to 98.6 wt. % of 2,4'-MDI, based on the weight of the MDI isomers. The distillation is preferably carried out at from 0.5 to 30 mbar, preferably at from 1 to 15 mbar absolute pressure. For the distillation, a column containing at least 1, preferably at least 5 and more preferably at least 10 theoretical plates is employed. Alternatively, the fraction from step e), if it has a content of 2,4'-MDI of more than 60 wt. %, based on the total weight of the MDI isomers, can also be purified by crystallisation. In this case, under partial crystallisation, the desired crystal phase is obtained with high contents of 2,4'-MDI and a mother liquor is obtained with high contents of 4,4'-MDI.

In step f), various 2-nuclear MDI mixtures with different contents of 2,4'-MDI and 4,4'-MDI can be obtained by distillation, and which have a very low content of 2,2'-MDI. Depending on the requirements, a moderately concentrated or a highly concentrated 2,4'-MDI product can, for example, be obtained batchwise in a distillation column. Alternatively, two or more distillation columns can also be operated in tandem, which permits a simultaneous production of the various 2-nuclear MDI mixtures.

Preferably, the fractions obtained in step f) contain from 0 to 0.35 wt. % of 2,2'-MDI, from 0.2 to 60 wt. % of 4,4'-MDI and from 40 to 99.8 wt. % of 2,4'-MDI, based on the total weight of the MDI isomers. It is more preferred to form a fraction which contains from 0 to 0.2 wt. % of 2,2'-MDI, from 0.5 to 55 wt. % of 4,4'-MDI and from 45 to 99.5 wt. % of 2,4'-MDI, based on the total weight of the MDI isomers. In step f), it is most preferred that a fraction is obtained which contains from 0 to 0.2 wt. % of 2,2'-MDI, from 0.5 to 10 wt. % of 4,4'-MDI and from 90 to 99.5 wt. % of 2,4'-MDI, based on the total weight of the MDI isomers, or that a fraction is obtained which contains from 0 to 0.2 wt. % of 2,2'-MDI, from 35 to 60 wt. % of 4,4'-MDI and from 40 to 65 wt. % of 2,4'-MDI, based on the total weight of the MDI isomers. In this connection, a purity of the MDI isomers in the fraction of >99.9 wt. % is achieved.

The content of solvents in the fraction obtained in step f) is preferably between 0 and 5 ppm, more preferably between 0 and 1 ppm and most preferably between 0 and 0.5 ppm, based on the weight of the MDI isomers. The content of phenyl isocyanate in the fraction obtained in step f) is preferably between 0 and 5 ppm, more preferably between 0 and 1 ppm and most preferably between 0 and 0.5 ppm, based on the weight of the MDI isomers.

The present invention also relates to a process for the production of very pure 2,4'-MDI, in which the fraction e) or the fraction f) containing from 30 to 70 wt. % of 4,4'-MDI is concentrated in a further isomer distillation to a very pure 2,4'-MDI which contains from 0 to 10% of 4,4'-MDI, preferably from 0 to 5% of 4,4'-MDI and more preferably from 0 to 3% of 4,4'-MDI, and contains from 0 to 1% of 2,2'-MDI, preferably from 0 to 0.5% of 2,2'-MDI and more preferably from 0 to 0.2% of 2,2'-MDI.

The present invention also relates to a process in which, for example, the steps d) and e), or the steps e) and f), and/or the step f), and the separation of the low boiling point compounds from the 2,2'-MDI fraction separated in step e), are carried out in a side stream column with three draw-off streams, with identical end product compositions finally being obtained. In this case, some of the intermediate products would simply not be specifically separated.

The present invention also relates to a process for the production of prepolymers or polyurethanes, in which pure 2,4'-MDI or the fraction produced in step e) or the fraction produced in step f) which contains from 0 to 0.5 wt. % of 2,2'-MDI, from 0.1 to 80 wt. % of 4,4'-MDI and from 20 to 99.9 wt. % of 2,4'-MDI, based on the total weight of the MDI isomers, is reacted with polyethers or polyesters.

All ranges used throughout the present application are inclusive of upper and lower limits, unless otherwise stated. All ranges provided may also use any combination of upper and lower limits, inclusive, unless otherwise stated.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The process according to the present invention is described hereinafter with the aid of examples. In this connection, all % figures refer to % by weight (wt. %).

For the production of 2,2'-MDI-containing and 2,4'-MDI-containing isomer mixtures, an MDA base (i.e. diamines and polyamines of the diphenylmethane series) is first of all conventionally prepared from aniline and formaldehyde solution. The MDA base is then phosgenated, and separated by distillation into a monomer fraction and a polymer fraction. The monomer fraction thereby obtained (i.e. 2-nuclear MDI) is separated by distillation into the isomers. The specified analysis results of the MDI isomers, as well as of the secondary products monochlorobenzene and phenyl isocyanate, were measured by gas chromatography. The HC content of hydrolyzable chlorine was determined by titration.

Example 1 (Not According to the Invention)

In step a), 1,000 g of aniline were mixed with 306 g of 31.9% aqueous HCl in a stirred vessel at 40° C. 480 g of 32% formaldehyde solution were added dropwise thereto over 15 minutes. The mixture was first stirred for a further 15 minutes at 40° C., and then the temperature was slowly raised to 100° C. within the next 2.5 hours. The reaction mixture was then stirred under reflux for 10 hours at 100° C. and neutralised with 50% sodium hydroxide solution, the aqueous phase was separated, and the organic phase was washed with water. The organic solution was removed and freed from excess aniline by distillation in vacuo.

In step b), the MDA reaction product was poured into an ice-cold 15% solution of phosgene in monochlorobenzene (MCB) that was previously placed in a second stirred vessel; the molar excess of phosgene was 200%. The reaction solution was slowly heated within 1 hour to 100° C. under constant addition of 40 liters/hour of phosgene. The mixture was brought to boiling point within a further hour, the addition of phosgene was stopped, and a vacuum was applied. The temperature was raised stepwise to 210° C., the pressure was reduced to 3 mbar absolute, and the solvent was completely removed. A crude MDI mixture was formed. This crude MDI mixture contained 58 wt. % of monomeric MDI, based on the total weight of the MDI isomers and oligomers.

The crude MDI fraction obtained in b) was then separated in step c) into the polymeric MDI product, as well as the monomer fraction (i.e. 2-nuclear MDI). The experimental apparatus consisted of a glass vessel with a droplet separator packing in the vapor space. The distillate was stripped via the head of the column, and was completely precipitated and removed. The pressure was adjusted to 5 mbar absolute. The crude MDI mixture was fed at 180° C. to the continuously operating apparatus. The following compositions of the products were measured under stationary equilibrium conditions:

Bottom: a polymeric MDI mixture which had a viscosity of 185 mPas at 25° C.

Head stream of the distillation apparatus [=fraction c)]:

Comprised 0.54% of 2,2'-MDI, 11.29% of 2,4'-MDI, and 88.17% of 4,4'-MDI, based on the total weight of MDI isomers.

The above fraction c) formed the starting mixture for the following isomer separation.

The fraction c) was fed, in step d), to a continuously operating laboratory packed column (isomer distillation) with 10 theoretical plates in both the stripping part and ascending part. The pressure was adjusted to 3 mbar at the head of the column. The feed temperature was 175° C. The product distilled overhead was condensed at 100° C. by a condenser. The condensed MDI was partly recycled to the distillation via a distributor, and the remainder was removed as distillate fraction. With a reflux ratio (reflux/distillate) of 7 and a removal of 20% of the feed as distillate and 80% as bottom product, a bottom composition was obtained which contained 0% of 2,2'-MDI, 1.4% of 2,4'-MDI and 98.6% of 4,4'-MDI. The fraction d) reached a distillate quality of 2.2% of 2,2'-MDI, 41.9% of 2,4'-MDI and 55.9% of 4,4'-MDI, with the weight basis for both being the total weight of the MDI isomers.

This distillate fraction d) was fed to a further glass column for distillation. This glass column comprised 10 theoretical plates in both the stripping part and enrichment part. The fraction d) was, in this step e), continuously metered in at 175° C. between the stripping part and enrichment part. At 3 mbar absolute, 6% of the feed was removed overhead with a reflux ratio of 12. A distillate phase was formed which contained 18.4% of 2,2'-MDI, 70.6% of 2,4'-MDI and 11.0% of 4,4'-MDI, based on the total weight of the MDI isomers. The distillate phase in addition contained 0.3% of organic compounds derived from secondary products formed in the MDI production. The bottom fraction e) had the following composition: 1.2% of 2,2'-MDI, 40.1% of 2,4'-MDI and 58.7% of 4,4'-MDI, based on the total weight of the MDI isomers.

The fraction e) was highly purified by distillation in the final step f), and was separated in a further glass column with 10 theoretical plates in both the stripping part and enrichment part. The fraction e) was continuously metered in at 175° C. between the stripping part and enrichment part. At 3 mbar absolute, ⅔ of the feed was removed overhead at a reflux ratio of 1. A distillate phase was formed that contained 1.79% of 2,2'-MDI, 52.74% of 2,4'-MDI and 45.47% of 4,4'-MDI, based on the total weight of the MDI isomers, as well as 1 ppm of monochlorobenzene, 1 ppm of phenyl isocyanate and 10 ppm of hydrolysable chlorine. The resulting bottom phase was combined with the crude MDI mixture, i.e. the fraction b) in Example 1, and was recycled to the steps c) to f).

Example 2 (According to the Invention)

The process as described above in Example 1 was followed through the completion of step d). From this point on, Example 2 varied from Example 1 as described below.

The distillate fraction d) from Example 1 was fed in step e) to a further isomer separation by distillation. This glass column contained 10 theoretical plates in the enrichment part and 20 theoretical plates in the stripping part (packing underneath the feed distributor). The fraction d) was metered in continuously at 175° C. between the stripping part and enrichment part. At 3 mbar absolute, 6% of the feed was withdrawn overhead at a reflux ratio of 10. A distillate phase was obtained which contained 36.8% of 2,2'-MDI, 62.4% of 2,4'-MDI and 0.8% of 4,4'-MDI, based on the total weight of the MDI isomers. The distillate phase also contained 0.3% of organic compounds derived from secondary products formed in the MDI production. The bottom fraction e) had the following composition: 0.05% of 2,2'-MDI, 40.65% of 2,4'-MDI and 59.3% of 4,4'-MDI, based on the total weight of the MDI isomers.

The fraction e) was then highly purified by distillation in the final step f), and was separated in a further glass column containing 10 theoretical plates in both the stripping part and enrichment part. The fraction e) was continuously metered in at 175° C. between the stripping part and enrichment part. At 3 mbar absolute, ⅔ of the feed was withdrawn at a reflux ratio of 1 (distillate stream=reflux stream). A distillate phase, the fraction f), was formed as target product, and it contained 0.07% of 2,2'-MDI, 52.52% of 2,4'-MDI and 47.41% of 4,4'-MDI, based on the total weight of the MDI isomers, as well as 0.2 ppm of monochlorobenzene, 0.1 ppm of phenyl isocyanate and 7 ppm of hydrolysable chlorine. The resulting bottom phase was combined with the crude MDI mixture, the fraction b) in Example 1, and was recycled to the steps c) to f).

Example 3 (Not According to the Invention)

The fraction e) from Example 1 was highly purified by distillation in step f), and was separated in a further glass column containing 10 theoretical plates in both the stripping part and enrichment part. The fraction e) was continuously metered in at 175° C. between the stripping part and enrichment part. At 3 mbar absolute, 35% of the feed was removed overhead at a reflux ratio of 2 (distillate stream=reflux stream). A distillate phase, the fraction f), was formed as target product, which contained 3.37% of 2,2'-MDI, 95.12% of 2,4'-MDI and 1.51% of 4,4'-MDI, based on the total weight of the MDI isomers. The resulting bottom phase was combined with the crude MDI mixture, the fraction b) in Example 1, and was recycled to the steps c) to f).

Example 4 (According to the Invention)

The fraction e) from Example 2 was now highly purified by distillation in the final step f). For this purpose, a further glass column was used which contained 10 theoretical plates in both stripping part and enrichment part. The fraction e) was metered in continuously at 175° C. between the stripping part and enrichment part. At 3 mbar absolute, 30% of the feed was removed overhead at a reflux ratio of 2. A distillate phase, the fraction f), was formed as target product, and it contained 0.16% of 2,2'-MDI, 97.05% of 2,4'-MDI and 2.79% of 4,4'-MDI, based on the total weight of the MDI isomers. The resulting bottom phase was combined with the crude MDI mixture, i.e. the fraction b) in Example 1, and was recycled to the steps c) to f).

TABLE 1

Analysis data of the produced fractions from process step f) of Examples 1-4 in wt. %, according to gas chromatography analysis.

| | Example No. | | | |
|---|---|---|---|---|
| | 1 | 2 | 3 | 4 |
| 2,2'-MDI | 1.79 | 0.07 | 3.37 | 0.16 |
| 2,4'-MDI | 52.74 | 52.52 | 95.12 | 97.05 |
| 4,4'-MDI | 45.47 | 47.41 | 1.51 | 2.79 |

Example 5 (According to the Invention)

The end product from Example 2, the distillation fraction f), was concentrated by distillation in a further step to form a very pure 2,4'-MDI fraction. For this purpose, a glass column was used which contained 10 theoretical plates in both the stripping part and enrichment part. The fraction f) from Example 2 was continuously metered in at 175° C. between the stripping part and enrichment part. At 3 mbar absolute, 50% of the feed was withdrawn overhead at a reflux ratio of 2. A distillate phase, the fraction f), was obtained as target product, which contained 0.15% of 2,2'-MDI, 96.86% of 2,4'-MDI and 2.99% of 4,4'-MDI, based on the total weight of the MDI isomers. The resulting bottom phase was combined with the crude MDI mixture, the fraction b) in Example 1, and was recycled to the steps c) to f).

Example 6 (According to the Invention)

The distillate fraction e) from Example 2 was purified by distillation in a further step to form a usable MDI fraction g). For this purpose, a glass column was used which contained 10 theoretical plates in both the stripping part and enrichment part. The distillate fraction from step e) of Example 2 was metered in continuously at 175° C. between the stripping part and enrichment part. At 3 mbar absolute, 20% of the feed was removed overhead at a reflux ratio of 5. A bottom phase, the fraction g), was formed as target product, which contained 28.2% of 2,2'-MDI, 70.9% of 2,4'-MDI and 0.9% of 4,4'-MDI, based on the weight of the MDI isomers. The resulting distillate phase contained, in addition to the main constituent 2,2'-MDI, very many low boiling point secondary components of the MDI production and was passed to the thermal utilisation unit.

The above examples demonstrate that, by using an extremely multistage stripping part in the separating column of the process step e), the 2,2'-MDI concentration in the MDI isomer mixture can be minimised. The product from an isomer separation column improved in this way can be used for the production of MDI isomer mixtures which are largely free from 2,2'-isomer such as, for example, for production of a very pure 2,4'-product or for production of a mixture of 2,4'-isomer and 4,4'-isomer in the vicinity of the eutectic mixed point. It is also shown that the separated 2,2'-rich MDI mixture can be freed, by repeated distillation, from the interfering low boiling point compounds, and can be made available for polyurethane production, and in this way, its combustion can be minimised and the MDI yield can be raised.

Example 7 describes, by means of an exemplary application, the improved properties of polyurethane systems based on MDI products with a high 2,4'-MDI content and a minimised 2,2'-MDI content.

Example 7

This example was an application example for the high 2,4'-MDI content MDI products produced according to the invention in Examples 1-4 (with minimised 2,2'-MDI content) and products produced not according to the invention. An adhesive for two films was produced and the emission of residual monomers from the composite was used as a measure of the reactivity. It is preferred by film composite manufacturers for the emissions overall to be as low as possible and the storage time required for full completion of the reaction to be as short as possible.

Production of Prepolymer I:

515 g of an isocyanate-reactive material, commercially available as Desmophen 1112 BD® (from Bayer AG), with an hydroxyl number of 112 mg KOH/g and a water content of 0.03 wt. % were added, under nitrogen at 60° C., to 486 g of a diphenylmethane diisocyanate produced according to Example 1 which had the following composition:

52.74 wt. % of 2,4'-diphenylmethane diisocyanate,
1.79 wt. % of 2,2'-diphenylmethane diisocyanate, and
45.47 wt. % of 4,4'-diphenylmethane diisocyanate.

After the slightly exothermic reaction died down, the reaction was brought to completion at 75° C. After 7 hours, a constant isocyanate content was obtained. Analysis data:

| | |
|---|---|
| NCO content (wt. %): | 11.68 |
| Viscosity at 25° C. (mPas): | 5210 |
| Content of 2,2'-MDI (wt. %): | 0.8 |
| Content of 2,4'-MDI (wt. %): | 14.9 |
| Content of 4,4'-MDI (wt. %): | 8.7 |

Production of Prepolymer II 515 g of an isocyanate-reactive material, commercially available as Desmophen 1112 BD® (from Bayer AG), with an hydroxyl number of 112 mg KOH/g and a water content of 0.03 wt. %, were added under nitrogen at 60° C., to 486 g of a diphenylmethane diisocyanate produced by the process according to the invention as described in Example 2 above, which had the following composition:

52.52 wt. % of 2,4'-diphenylmethane diisocyanate,
0.07 wt. % of 2,2'-diphenylmethane diisocyanate, and
47.41 wt. % of 4,4'-diphenylmethane diisocyanate.

After the slightly exothermic reaction died down, the reaction was brought to completion at 75° C. After 7 hours, a constant isocyanate content was obtained. Analysis data:

| | |
|---|---|
| NCO content (wt. %): | 11.71 |
| Viscosity at 25° C. (mPas): | 4180 |
| Content of 2,2'-MDI (wt. %): | <0.05 |
| Content of 2,4'-MDI (wt. %): | 15.1 |
| Content of 4,4'-MDI (wt. %): | 9.5 |

Production of Prepolymer III:

515 g of an isocyanate-reactive material, commercially available as Desmophen 1112 BD® (from Bayer AG), with an hydroxyl number of 112 mg KOH/g and a water content of 0.03 wt. %, were added under nitrogen at 60° C., to 486 g of a diphenylmethane diisocyanate produced according to Example 3 and which had the following composition:

95.12 wt. % of 2,4'-diphenylmethane diisocyanate,
3.37 wt. % of 2,2'-diphenylmethane diisocyanate, and
1.51 wt. % of 4,4'-diphenylmethane diisocyanate.

After the slightly exothermic reaction died down, the reaction was brought to completion at 75° C. After 7 hours, a constant isocyanate content was obtained. Analysis data:

| | |
|---|---|
| NCO content (wt. %): | 11.81 |
| Viscosity at 25° C. (mPas): | 4310 |
| Content of 2,2'-MDI (wt. %): | 1.2 |
| Content of 2,4'-MDI (wt. %): | 22.7 |
| Content of 4,4'-MDI (wt. %): | <0.05 |

Production of Prepolymer IV:

515 g of an isocyanate-reactive material, commercially available as Desmophen 1112 BD® (from Bayer AG), with an hydroxyl number of 112 mg KOH/g and a water content of 0.03 wt. % were added under nitrogen at 60° C., to 486 g of a diphenylmethane diisocyanate produced by the process according to the invention as described in Example 4, and which had the following composition:

97.05 wt. % of 2,4'-diphenylmethane diisocyanate,
0.16 wt. % of 2,2'-diphenylmethane diisocyanate, and
2.79 wt. % of 4,4'-diphenylmethane diisocyanate.

After the slightly exothermic reaction died down, the reaction was brought to completion at 75° C. After 7 hours, a constant isocyanate content was obtained. Analysis data:

| | |
|---|---|
| NCO content (wt. %): | 11.74 |
| Viscosity at 25° C. (mPas): | 4440 |
| Content of 2,2'-MDI (wt. %): | 0.05 |
| Content of 2,4'-MDI (wt. %): | 23.0 |
| Content of 4,4'-MDI (wt. %): | 0.4 |

Production of a Polyol Mixture:

1000 g of an isocyanate-reactive material, commercially available as Baycoll AD 1115 ® (from Bayer AG), with an hydroxyl number of 113.3 mg KOH/g, acid number of 0.8 mg KOH/g and a water content of 0.03 wt. %, and 80 g of trimethylolpropane were intensively mixed together. The polyol mixture that was thereby formed had a hydroxyl number (mg KOH/g) of 196.7.

Production of Polyurethane Reaction Mixtures and Composite Films:

A polyurethane reaction mixture was produced by mixing together 50 g of the polyol mixture and the amount of prepolymer as specified in Table 2. These amounts correspond to a characteristic number (NCO/OH or Isocyanate Index) of about 140. The polyurethane reaction mixtures were intensively mixed for 2 minutes with a wooden spatula and then added to the roller gap of a Polytest 440 laboratory laminating machine.

TABLE 2

Production of polyurethane reaction mixtures A-D

| PUR Reaction Mixture for Composite | Amount (g) of the Prepolymer | | Amount (g) of the Polyol Mixture |
|---|---|---|---|
| A | 88.3 | I | 50 |
| B | 88.0 | II | 50 |
| C | 86.9 | III | 50 |
| D | 87.8 | IV | 50 |

The roller temperature was ca. 30° C. and the coating rate was ca. 10 m/min. The film width was 30 cm. The following film composite was produced. The aluminium side of a polyester/aluminium precomposite was bonded using a lubricant to low density polyethylene (LDPE) of the type LDPE-K-088 (70µ layer thickness), which had been treated with a corona to improve the adhesiveness on the side being bonded. The amount of polyurethane reaction mixture applied is given in Table 3.

Testing of the Composite Strengths

The choice of test samples was made from an at least 20 m long laminate of 30 cm strip width tightly wound round a sleeve. The test samples were, in each case, cut out from the middle of the composite film strip after unwinding a length corresponding to 5 windings. From the time of the production on, the composite films were stored in a thermostatically controlled room at 23° C. and 50% atmospheric humidity.

The composite strengths were tested in each case 24 hours, 3 days, 7 days and 14 days after the production of the composite films. For this purpose, 15 mm-wide strips of the laminates were cut with impact shears parallel to the edge into ca. 30 cm lengths. The composite testing was carried out as a T-peeling test in accordance with DIN 53289 using a VNGG test machine from Brugger, Munich, at a 100 mm/min stripping rate, on a length of at least 10 cm. The data were given as Newtons/15 mm. All results were mean values of double determinations.

TABLE 3

Results of the testing of the composite strengths

| Composite | Reaction mixture according to Table 2 | Applied Weight (g/m$^2$) | Composite strengths in Newtons/15 mm after following days | | | | | | |
|---|---|---|---|---|---|---|---|---|---|
| | | | 1 | 2 | 3 | 7 | 14 | 21 | 28 |
| A | I | 2.8 | 5.6 | 8.8 | 10.3 | 10.8 | 10.8 | 11.8 D | 11.3 D |
| B | II | 3.0 | 5.0 | 9.2 | 10.0 | 9.2 | 11.0 | 11.6 D | 11.9 D |
| C | III | 3.0 | 4.9 | 9.8 | 10.5 | 9.7 | 11.2 D | 11.2 D | 12.3 D |
| D | IV | 3.2 | 4.5 | 7.9 | 10.2 | 10.0 | 10.2 | 10.4 D | 12.5 A |

D = Extension of the film;
A = Tearing off of the film

Migration Investigations

The determination of the migration values of aromatic polyamines was carried out according to the method published in "Amtliche Sammlung von Untersuchungs-verfahren nach § 35 LBMG L.00.00-6" ["Official Collection of Investigation Methods According to § 35 LBMG L.00.00-6"].

The film composites to be investigated were stored, wound on the sleeve, in a thermostatically controlled room at 23° C. and 50% relative humidity. 10 windings of film strip were unwound in each case, after 1, 3, 7 and 14 days and two pieces of film were removed from each. The pieces of film were sealed so as to form a bag having a contact area of 2 $dm^2$ for the test foodstuff.

The bags were filled with 100 ml of 3% acetic acid preheated to 70° C., sealed, and stored for 2 hours at 70° C. Immediately after storage, the bags were emptied and the test foodstuff was cooled to room temperature.

The polyisocyanates that have migrated were detected by diazotisation of the aromatic amines present in the test foodstuff, followed by coupling with N-(1-naphthyl)ethylenediamine. The diazo dye that was formed, was then concentrated on a separating column, eluted, and the extinction values were measured at 550 nm in a photometer. The values were converted into μg anilinium hydrochloride/100 ml of test foodstuff with the aid of a calibration curve. The detection limit was given as 0.2 μg anilinium hydrochloride/100 ml.

The specified values were mean values based on three measurements.

TABLE 4

Results of the migration value tests:

| Com-posite | Amount of Amine Found (in μg anilinium hydrochloride/100 ml) after the following days | | | | | |
|---|---|---|---|---|---|---|
| | 1 | 3 | 7 | 14 | 28 | 42 |
| A | 14.8 | 2.7 | 1.35 | 0.83 | 1.23 | 1.0 |
| B | 11.3 | 0.83 | <0.2 | <0.2 | <0.2 | <0.2 |
| C | 8.2 | 1.87 | 0.95 | 0.67 | 0.97 | 0.93 |
| D | 3.9 | 0.5 | <0.2 | <0.2 | <0.2 | <0.2 |

Table 4 shows that, in the film composites that have been produced with MDI mixtures which have high contents of 2,4'-MDI (i.e. Composites C and D), lower contents of aromatic amines were found after 1 day and after 3 days than with, in each case, the comparable film composites (i.e. those which contain comparable amounts of 2,2'-MDI) that were produced with MDI mixtures having low contents of 2,4'-MDI (i.e. Composites A and B). On account of the comparable contents of 2,2'-MDI in the prepolymer that is used, it is thus possible to make a direct comparison of the film composites A and C, as well as B and D.

In addition, Table 4 shows that the film composites that were produced with MDI prepolymers with low contents of 2,2'-MDI (i.e. composites B and D) were, after 7 days, largely free of aromatic amines (i.e. below the detection limit in this test). On the other hand, in the film composites that were produced with MDI prepolymers with high contents of 2,2'-MDI (i.e. composites A and C), aromatic amine concentrations above the detection limit were also found, even after 42 days.

It is thus evident that the fractions of diisocyanates of the diphenylmethane series produced by the process according to the invention (i.e. the MDI fractions on which the composite films B and D were based) which have low contents of 2,2'-MDI, have superior product properties in applications compared to the diisocyanates of the diphenylmethane series produced according to the prior art (i.e. the MDI fractions on which the composite films A and C were based) which have high contents of 2,2'-MDI.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a fraction of diisocyanates of the diphenylmethane series which contains at least 99 wt. % of 2-nuclear methylenediphenyl diisocyanate (based on the total weight of the fraction), comprising
    a) reacting aniline and formaldehyde in the presence of an acid catalyst to form diamines and polyamines of the diphenylmethane series containing 2-nuclear methylenediphenyldiamine,
    b) phosgenating the 2-nuclear methylenediphenyldiamine containing diamines and polyamines of the diphenylmethane series, optionally in the presence of a solvent, to yield a crude diisocyanate and polyisocyanate,
    c) separating from the crude diisocyanate and polyisocyanate a fraction which containing at least 95 wt. % of 2-nuclear methylenediphenyl diisocyanate having a content of 4,4'-MDI of from 49 to 95.99 wt. %, a content of 2,4'-MDI of from 4 to 45 wt. % and a content of 2,2'-MDI of from 0.01 to 20 wt. %, based on the total weight of the fraction,
    d) optionally, removing from 10 to 98% of 4,4'-MDI from the fraction obtained in step c),
    e) separating from 50 to 99.9999% of the 2,2'-MDI from the fraction obtained in step c), thereby forming a fraction containing from 0 to 0.4 wt. % of 2,2'-MDI, from 1 to 95 wt. % of 4,4'-MDI and from 5 to 98.6 wt. % of 2,4'-MDI, based on the total weight of the MDI isomers.

2. The process of claim 1 further comprising
    f) separating a fraction that contains at least 99 wt. % of 2-nuclear methylenediphenyl diisocyanate, based on the total weight of the fraction, and which contains from 0 to 0.5 wt. % of 2,2'-MDI, from 0.1 to 80 wt. % of 4,4'-MDI and from 20 to 99.9 wt. % of 2,4'-MDI, based on the total weight of the MDI isomers, from the fraction formed in e) which contains from 0 to 0.4 wt. % of 2,2'-MDI, from 1 to 95 wt. % of 4,4'-MDI and from 5 to 98.6 wt. % of 2,4'-MDI, based on the total weight of the MDI isomers.

3. The process of claim 1, in which the separation in step c) forms a fraction containing at least 98 wt. % of 2-nuclear methylenediphenyl diisocyanate which has a content of 4,4'-MDI of from 80 to 93.9 wt. %, a content of 2,4'-MDI of from 6 to 19.9 wt. % and a content of 2,2'-MDI of from 0.1 to 5 wt. %, based on the total weight of the fraction.

4. The process of claim 1, in which in step d) the 4,4'-MDI is removed from the fraction in a distillation step or in a crystallisation step.

5. The process of claim 4, in which in step d) from 50 to 95% of the 4,4'-MDI is removed from the fraction.

6. The process of claim 1, in which the 2,2'-MDI separated in step e) is purified by crystallisation or distillation from low boiling point compounds, thereby forming an isomer mixture containing from 5 to 99.99 wt. % of 2,2'-MDI, from 0 to 50 wt. % of 4,4'-MDI and from 0.01 to 95 wt. % of 2,4'-MDI, based on the total weight of the MDI isomers.

7. The process of claim 6, in which the resultant isomer mixture which contains from 5 to 99.99 wt. % of 2,2'-MDI, from 0 to 50 wt. % of 4,4'-MDI and from 0.01 to 95 wt. % of 2,4'-MDI, based on the total weight of the MDI isomers, is optionally mixed with other fractions containing isocyanate, and then reacted with polyethers or polyesters to form polyurethanes or prepolymers.

8. The process of claim 1, in which step e) forms a fraction containing from 0 to 0.3 wt. % of 2,2'-MDI, from 5 to 85 wt. % of 4,4'-MDI and from 15 to 95 wt. % of 2,4'-MDI, based on the total weight of the MDI isomers.

9. The process of claim 2, in which the separation in step f) is by distillation carried out at 0.5 to 30 mbar absolute pressure.

10. The process of claim 9, in which the distillation is carried out 1 to 15 mbar absolute pressure.

11. The process of claim 2, in which step f) forms a fraction is is containing from 0 to 0.35 wt. % of 2,2'-MDI, from 0.2 to 60 wt. % of 4,4'-MDI and from 40 to 99.8 wt. % of 2,4'-MDI, based on the total weight of the MDI isomers.

12. The process of claim 2, in which step f) forms a fraction containing from 0 to 0.2 wt. % of 2,2'-MDI, from 0.5 to 55 wt. % of 4,4'-MDI and from 45 to 99.5 wt. % of 2,4'-MDI, based on the total weight of the MDI isomers.

13. The process of claim 1, in which the steps d) and e) are carried out simultaneously in a common distillation step.

14. The process of claim 13, in which the common distillation step is carried out in a side stream column.

15. The process of claim 2, in which steps e) and f) are carried out simultaneously in a common distillation step.

16. The process of claim 15, in which the common distillation step is carried out in a side stream column.

17. The process of claim 6, in which the separation in step f) and the separation of the low boiling point compounds from the 2,2'-MDI in step e) are carried out simultaneously in a common distillation step.

18. The process of claim 17, in which the common distillation step is carried out in a side stream column.

\* \* \* \* \*